US008827911B2

(12) United States Patent
Tsuji et al.

(10) Patent No.: US 8,827,911 B2
(45) Date of Patent: Sep. 9, 2014

(54) APPARATUS AND METHOD OF EVALUATING VASCULAR ENDOTHELIAL FUNCTION (75) Inventors: Toshio Tsuji, Hiroshima (JP); Masao Yoshizumi, Hiroshima (JP); Yukihito Higashi, Hiroshima (JP); Masashi Kawamoto, Hiroshima (JP); Teiji Ukawa, Tokyo (JP)

(73) Assignees: Nihon Kohden Corporation, Tokyo (JP); Hiroshima University, Hiroshima (JP)

( * ) Notice: Subject to any disclaimer, the term of this patent is extended or adjusted under 35 U.S.C. 154(b) by 1261 days.

(21) Appl. No.: 12/423,295

(22) Filed: Apr. 14, 2009

(65) Prior Publication Data

US 2009/0259131 A1    Oct. 15, 2009

(30) Foreign Application Priority Data

Apr. 14, 2008  (JP) .............................. P.2008-104759
Dec. 18, 2008  (JP) .............................. P. 2008-322586

(51) Int. Cl.
*A61B 5/02*    (2006.01)
*A61B 5/021*   (2006.01)
*A61B 5/022*   (2006.01)

(52) U.S. Cl.
CPC .............. *A61B 5/022* (2013.01); *A61B 5/02116* (2013.01); *A61B 5/02007* (2013.01)
USPC ........... 600/483; 600/481; 600/485; 600/490; 600/500

(58) Field of Classification Search
USPC ......... 600/485, 488, 490, 492–496, 500–502, 600/300–301, 481, 483, 504, 507
See application file for complete search history.

(56) References Cited

U.S. PATENT DOCUMENTS

| | | | |
|---|---|---|---|
| 5,724,981 A * | 3/1998 | Apple | 600/493 |
| 6,319,205 B1 * | 11/2001 | Goor et al. | 600/485 |
| 2004/0092832 A1 * | 5/2004 | Schnall et al. | 600/490 |
| 2005/0070805 A1 | 3/2005 | Dafni | |

FOREIGN PATENT DOCUMENTS

| | | |
|---|---|---|
| EP | 1992282 A1 | 11/2008 |
| JP | 03-070489 B2 | 11/1991 |
| JP | 04-059890 B2 | 9/1992 |
| JP | 3632014 B2 | 12/2004 |
| JP | 2006-181261 A | 7/2006 |
| JP | 2007-209492 A | 8/2007 |
| WO | 2007/097654 A1 | 8/2007 |

OTHER PUBLICATIONS

European Search Report dated Sep. 4, 2009.
Communication from the Japanese Patent Office dated Jan. 31, 2013, in a counterpart application No. 2008-322586.

* cited by examiner

*Primary Examiner* — Michael D'Angelo
(74) *Attorney, Agent, or Firm* — Sughrue Mion, PLLC (57) ABSTRACT An apparatus for evaluating a vascular endothelial function includes: a cuff, to be wound around a part of a body of a subject; a cuff pressure controller, configured to control a pressure of the cuff, and configured to apply continuous pressure stimulation; a cuff pressure detector, configured to detect the pressure of the cuff from output of a pressure sensor connected to the cuff; a pulse wave detector, configured to detect, from the output of the pressure sensor, pulse waves before and after the continuous pressure stimulation is applied; and an analyzer, configured to evaluate the vascular endothelial function by comparing the pulse waves detected before and after the continuous pressure stimulation is applied.

18 Claims, 10 Drawing Sheets

| MAXIMAL BLOOD PRESSURE | 165 mmHg |
|---|---|
| MINIMAL BLOOD PRESSURE | 95 mmHg |
| MEAN BLOOD PRESSURE | 110 mmHg |
| RATIO OF PULSE WAVE AMPLITUDES | 1.1 |

FIG. 5

CUFF PULSE WAVE AMPLITUDE

FIG. 6

RELATIVE CHANGE OF CUFF PULSE WAVE AMPLITUDE

FIG. 7
CUFF PULSE WAVE AMPLITUDE

FIG. 8
RELATIVE CHANGE OF CUFF PULSE WAVE AMPLITUDE

FIG. 9

|  | FIRST WEEK | SECOND WEEK | THIRD WEEK | FOURTH WEEK | FIFTH WEEK |
|---|---|---|---|---|---|
| MAXIMAL BLOOD PRESSURE | 165mmHg | 170mmHg | 130mmHg | 128mmHg | 125mmHg |
| MINIMAL BLOOD PRESSURE | 95mmHg | 98mmHg | 88mmHg | 78mmHg | 76mmHg |
| MEAN BLOOD PRESSURE | 110mmHg | 115mmHg | 98mmHg | 95mmHg | 93mmHg |
| RATIO OF PULSE WAVE AMPLITUDES | 1.05 | 1.06 | 1.11 | 1.38 | 1.45 |

FIG. 10

FIG. 11A
CASE WHERE PRESSURE IS REDUCED AT 5 mmHg/BEAT

FIG. 11B
CASE NO. 1 WHERE PRESSURE IS REDUCED AT 10 mmHg/BEAT

FIG. 11C
CASE NO. 2 WHERE PRESSURE IS REDUCED AT 10 mmHg/BEAT

APPARATUS AND METHOD OF EVALUATING VASCULAR ENDOTHELIAL FUNCTION

BACKGROUND OF THE INVENTION

The present invention relates to an apparatus and method of evaluating a vascular endothelial function in which the evaluation is enabled with a required minimum configuration by a simple measurement, without using an ultrasonic echo system or the like.

Recently, researches that arteriosclerosis develops while showing deterioration of the vascular endothelial function as the initial phase have been conducted. In order to prevent arteriosclerosis, techniques and apparatuses for evaluating the vascular endothelial function have been developed.

As a reliable technique for evaluating the vascular endothelial function, there is an apparatus called an FMD (Flow-Mediated Dilation) measurement system which is a related art. In the apparatus, measurement is performed in the following manner. A cuff which is similar to that for measuring the blood pressure is attached to the arm of the subject. After avascularization is performed for a constant time of about five minutes at a pressure which is higher than the maximal blood pressure of the subject, the avascularization is released. At about three minutes after the release of the avascularization, the vessel diameter at the upstream or downstream of the cuff is measured by an ultrasonic echo system. Based on the time-dependent change rate of the vessel diameter, the vascular endothelial function is evaluated.

In the case of a normal vessel, the production of NO which is a vasodepressor material from vascular endothelial cells is promoted by shear stress of the inner wall of the vessel due to a blood flow immediately after the avascularization. As a result, the vessel diameter is expanded. By contrast, in the case where a disorder exists in the vascular endothelial function, the degree of the expansion of the vessel diameter is decreased. When the change in vessel diameter before and after the avascularization is measured, therefore, it is possible to evaluate the vascular endothelial function.

The evaluation technique by the FMD measurement system requires skills in measurement of the vessel diameter by an ultrasonic echo system, and is difficult to handle. Furthermore, there is a problem in that the technique requires a large-scale apparatus and lacks in simplicity.

By contrast, as a technique using a simple configuration, there is a related-art technique using a cuff pressure. In the related-art technique, the cuff pressure is maintained at a predetermined pressure which is higher than the maximal blood pressure, thereafter rapidly lowered, maintained at another predetermined pressure which is higher than the minimal blood pressure and lower than the mean blood pressure, and, during when the cuff pressure is maintained at the other predetermined pressure, a ratio of a cuff pressure peak value of a first pulse wave which initially appears to the maximal cuff pressure peak value which thereafter appears is calculated, thereby enabling the vascular endothelial function to be evaluated (refer to JP-A-2007-209492).

As a technique in which an index of the vascular endothelial function can be accurately measured by a simple method, there is a related-art technique in which pressure and volume pulse waves of a vessel to be measured are measured, a ratio of variations of the pulse waves per unit time is obtained, and, with respect to the third root of the maximum value of the ratio of variations of one heartbeat cycle at rest, a ratio to a value after release of avascularization is calculated as the degree of vessel expansion (refer to JP-A-2006-181261).

There is a further related-art technique in which, based on the time-dependent change of posterior pulse wave information indicating a feature of the posterior half part which is after the peak of a pulse wave reflecting variations of the vessel diameter, it is determined whether the function of vascular endothelial cells is normal or not (refer to Japanese Patent No. 3632014).

In the related art disclosed in JP-A-2007-209492, the pressurizing periods for the pressure stimulation and the pulse wave measurement are continuous to each other. Although the pressure for the pulse wave measurement is lower than the artery mean blood pressure, the vein blood flow is blocked, and hence the burden on the subject is large.

In the related art disclosed in JP-A-2006-181261, in addition to the cuff for the pressure stimulation, a sensor for measuring the volume and pressure pulse waves must be disposed. Therefore, the operation is complicated.

In the related art disclosed in Japanese Patent No. 3632014, a reflected wave component which is contained in the pressure pulse wave, and which is originated from peripheral vessels is measured. Measurement of the reflected wave component and calculation of an amplitude augmentation factor AI necessitate complicated waveform recognizing and calculating processes, and an analyzing unit must have a high processing capacity.

The vascular compliance is changed by the blood pressure. When the blood pressure is high, the vessel wall is in a state where the wall is extended in the circumferential direction and hardened, and the compliance is low. Conversely, when the blood pressure is low, a force acting on the vessel wall is small. Therefore, the vessel wall is extended in a smaller degree in the circumferential direction, and the compliance is high. All of the related arts disclosed in JP-A-2007-209492, JP-A-2006-181261, and Japanese Patent No. 3632014 have a problem in that the measured vessel information is inevitably affected by the intravascular pressure, i.e., the blood pressure.

SUMMARY

It is therefore an object of the invention to provide an apparatus and method of evaluating a vascular endothelial function in which the configuration and the measurement technique are simplified, and the vascular endothelial function can be evaluated highly accurately.

In order to achieve the object, according to the invention, there is provided an apparatus for evaluating a vascular endothelial function, the apparatus comprising:

a cuff, to be wound around a part of a body of a subject;

a cuff pressure controller, configured to control a pressure of the cuff, and configured to apply continuous pressure stimulation;

a cuff pressure detector, configured to detect the pressure of the cuff from output of a pressure sensor connected to the cuff;

a pulse wave detector, configured to detect, from the output of the pressure sensor, pulse waves before and after the continuous pressure stimulation is applied; and an analyzer, configured to evaluate the vascular endothelial function by comparing the pulse waves detected before and after the continuous pressure stimulation is applied.

The analyzer may obtain an amplitude ratio between the pulse waves detected before and after the continuous pressure stimulation is applied.

The continuous pressure stimulation may be a constant pressure for a predetermined time period.

The cuff pressure controller may perform, at least one time, pressurizing processing that includes a first process and a second process subsequent to the first process, at least one of before and after applying the continuous pressure stimulation, the first process in which the pressure of the cuff is raised from a first pressure which is an atmosphere pressure to a second pressure which is equal to or higher than a maximal blood pressure of the subject, the second process in which the pressure of the cuff is lowered from the second pressure to a third pressure which is equal to or lower than a minimal blood pressure of the subject. The analyzer may apply statistical processing on variations of the pulse waves detected while the cuff pressure controller performs the pressurizing processing.

The statistical processing may be processing in which a maximum value in amplitudes of the pulse waves detected in the first process or the second process is obtained.

The statistical processing may be processing in which an average value of a neighborhood of a maximum value in amplitudes of the pulse waves detected while the cuff pressure controller performs the pressurizing processing is obtained.

The analyzer may perform processing in which an amplitude of each of the pulse waves is divided by a difference between a maximal blood pressure of the subject and a minimal blood pressure of the subject, to obtain vascular compliance.

The apparatus may further include a display. The analyzer may calculate a blood pressure value from each of the pulse waves. The display may display the blood pressure value together with a comparison result of the pulse waves.

In order to achieve the object, according to the invention, there is also provided a method of evaluating a vascular endothelial function by an apparatus, configured to control a pressure of a cuff to be wound around a part of a body of a subject and configured to detect the pressure of the cuff from output of a pressure sensor connected to the cuff, the method comprising:

applying continuous pressure stimulation;

detecting, from the output of the pressure sensor, pulse waves before and after the continuous pressure stimulation is applied; and evaluating the vascular endothelial function by comparing the pulse waves detected before and after the continuous pressure stimulation is applied.

The vascular endothelial function may be evaluated by obtaining an amplitude ratio between the pulse waves detected before and after the continuous pressure stimulation is applied.

The continuous pressure stimulation may be a constant pressure for a predetermined time period.

Pressurizing processing may be performed at least one time, at least one of before and after the continuous pressure stimulation is applied. The pressurizing processing includes a first process and a second process subsequent to the first process. In the first process, the pressure of the cuff is raised from a first pressure which is an atmosphere pressure to a second pressure which is equal to or higher than a maximal blood pressure of the subject. In the second process, the pressure of the cuff is lowered from the second pressure to a third pressure which is equal to or lower than a minimal blood pressure of the subject. Statistical processing may be applied on variations of the pulse waves detected while performing the pressurizing processing. A result of the statistical processing may be used for comparing the pulse waves detected before and after the continuous pressure stimulation is applied.

The statistical processing may be processing in which a maximum value in amplitudes of the pulse waves detected in the first process or the second process is obtained.

The statistical processing may be processing in which an average value of a neighborhood of a maximum value in amplitudes of the pulse waves detected while the pressurizing processing is performed is obtained.

The method may further include: performing processing in which an amplitude of each of the pulse waves is divided by a difference between a maximal blood pressure of the subject and a minimal blood pressure of the subject, to obtain vascular compliance.

The method may further include: calculating a blood pressure value from each of the pulse waves; and displaying the blood pressure value together with a comparison result of the pulse waves.

DETAILED DESCRIPTION OF PREFERRED EMBODIMENTS

Figure 1:
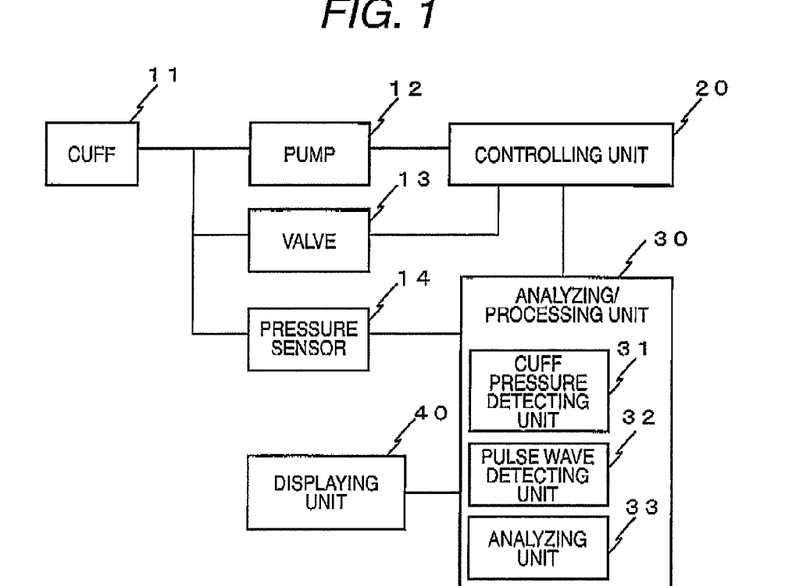
FIG. 1 is a diagram showing the configuration of an embodiment of an apparatus for evaluating a vascular endothelial function according to the present invention.

FIG. 1 is a diagram showing the configuration of an apparatus for evaluating a vascular endothelial function according to an embodiment of the invention. The apparatus includes a cuff 11, a pump 12, a valve 13, a pressure sensor 14, a controlling unit 20, an analyzing/processing unit 30, and a displaying unit 40. The cuff 11 is to be wound around a part of the body of the subject, and used for pressurizing the part of the body around which the cuff is wound.

The pump 12 feeds the air into the cuff 11 under the control of the controlling unit 20. The valve 13 switches inflating/deflating the cuff 11 under the control of the controlling unit 20. The controlling unit 20 includes a cuff pressure controlling unit which controls pressurization and depressurization of the cuff 11.

The pressure sensor 14 is connected to the cuff 11, and outputs a signal corresponding to the pressure in the cuff 11. The analyzing/processing unit 30 is configured by, for example, a computer, controls the whole apparatus, and includes a cuff pressure detecting unit 31, a pulse wave detecting unit 32, and an analyzing unit 33.

The cuff pressure detecting unit 31 detects the cuff pressure from an output of the pressure sensor 14. The pulse wave detecting unit 32 detects a pulse wave from the output of the pressure sensor 14. The analyzing unit 33 analyzes the detected pulse wave.

Figure 2A:
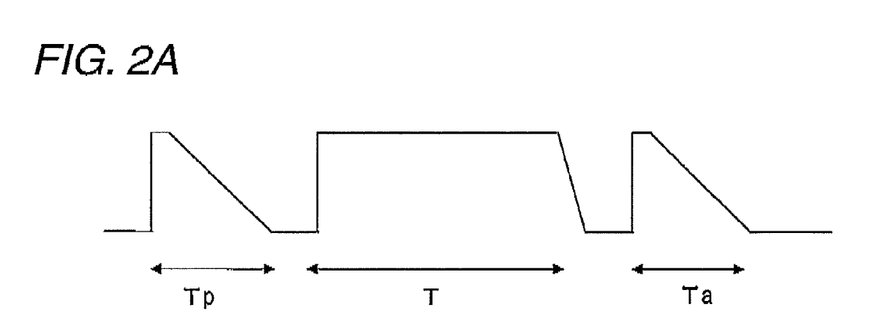
FIGS. 2A and 2B are views showing a first example of a pulse wave measurement which is performed by the embodiment of the apparatus, and an avascularization period.

The controlling unit 20 applies continuous pressure stimulation for a predetermined time period, on a part of the body of the subject, and changes the cuff pressure as shown in, for example, FIG. 2A. Namely, pressure stimulation of vascular endothelium is executed during a pressurization period T, and the pulse wave amplitude is measured before and after the pressurization period T, i.e., during pressurization periods Tp and Ta. For example, the pressurization period T may be set to about five minutes, and the pressurization periods Tp and Ta may be set to a time which is required for usual blood pressure measurement. During the pressurization period T, avascularization is performed at a pressure which is a sum of the maximal blood pressure and a predetermined pressure (for example, 50 mmHg).

Figure 3A:
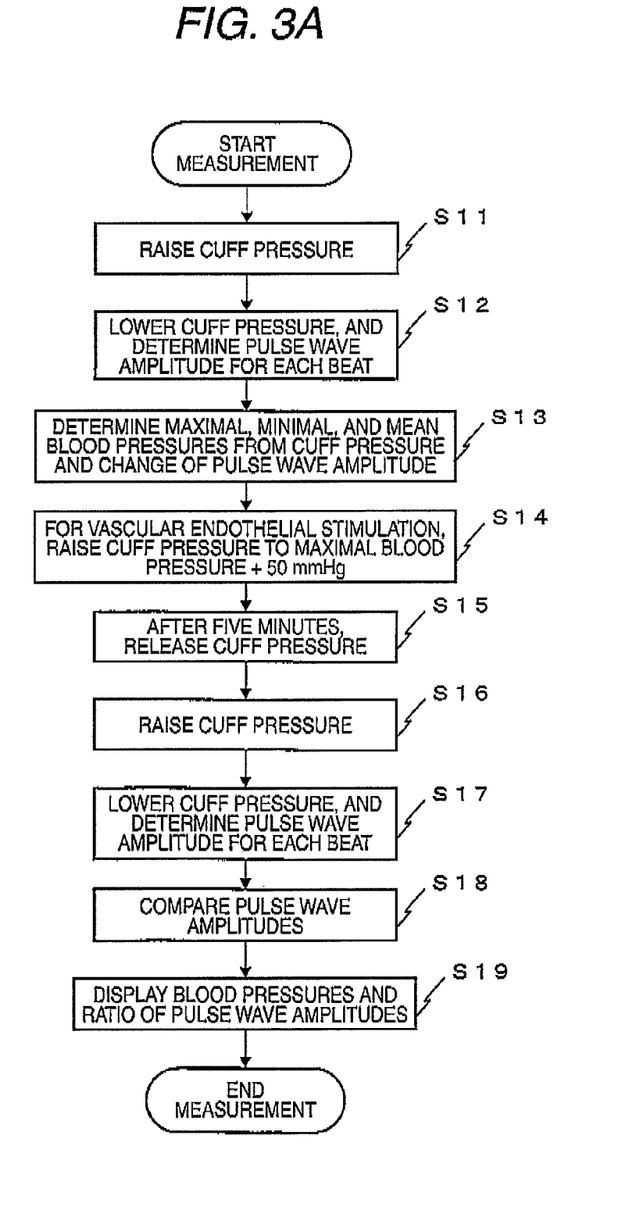
FIG. 3A is a flowchart illustrating a pulse wave measuring operation which is performed in a process of depressurizing a cuff pressure by the embodiment of the apparatus.

The apparatus for evaluating a vascular endothelial function performs processing shown in the flowchart of FIG. 3A. The cuff 11 is wound around a part of the body of the subject, and then the measurement is started. Under the control of the controlling unit 20, in a state where the valve 13 is closed, the air is sent from the pump 12 to the cuff 11 to raise the cuff pressure (S11).

When the cuff pressure reaches a predetermined pressure, the air supply from the pump 12 is stopped, and the valve 13 is opened. Therefore, the cuff pressure is lowered, and the pulse wave detecting unit 32 detects the pulse wave amplitude for each beat (S12).

Figure 2B:
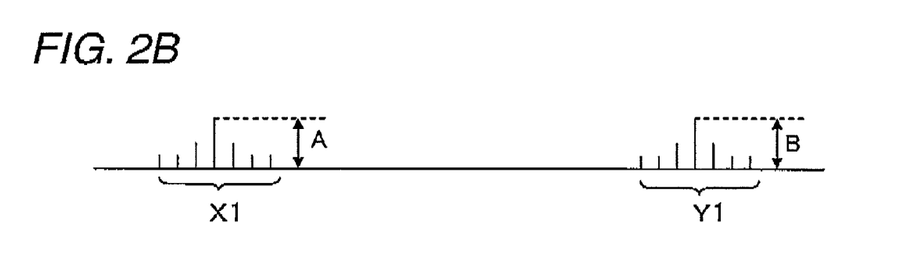

Furthermore, the cuff pressure detecting unit 31 detects the cuff pressure from the output of the pressure sensor 14, and, on the basis of the cuff pressure and the pulse wave amplitude, the analyzing unit 33 determines the maximal, minimal, and mean blood pressures, and obtains a representative pulse wave amplitude (S13). The representative pulse wave amplitude is obtained by statistically processing the pulse wave amplitude which is obtained in the pressurization period Tp. The pulse wave amplitude in the pressurization period Tp is obtained as shown in FIG. 2B, and hence the maximum pulse wave amplitude A is obtained. In the pressurization period Tp, when the cuff pressure is equal to the mean blood pressure, the pulse wave amplitude is maximum, and the amplitude is set as the maximum pulse wave amplitude A.

Next, the pressurization period T when, for vascular endothelial stimulation, avascularization is performed at a pressure which is a sum of the maximal blood pressure and the predetermined pressure (for example, 50 mmHg) is realized (S14). After five minutes, the cuff pressure is released, and the cuff pressure is lowered to a pressure which is equal to or lower than the minimal blood pressure (S15). Thereafter, the cuff pressure is raised (S16). Furthermore, the cuff pressure is lowered in a similar manner as described above, and the pulse wave detecting unit 32 detects the pulse wave amplitude for each beat (S17).

In a similar manner as step S13, on the basis of the cuff pressure and the pulse wave amplitude, the analyzing unit 33 determines the maximal, minimal, and mean blood pressures, and obtains a representative pulse wave amplitude B (S17). The representative pulse wave amplitude A and the representative pulse wave amplitude B are compared with each other to evaluate the vascular endothelial function (S18). The comparison is performed by obtaining a result of a division in which the representative pulse wave amplitude B is divided by the representative pulse wave amplitude A.

Figure 3B:
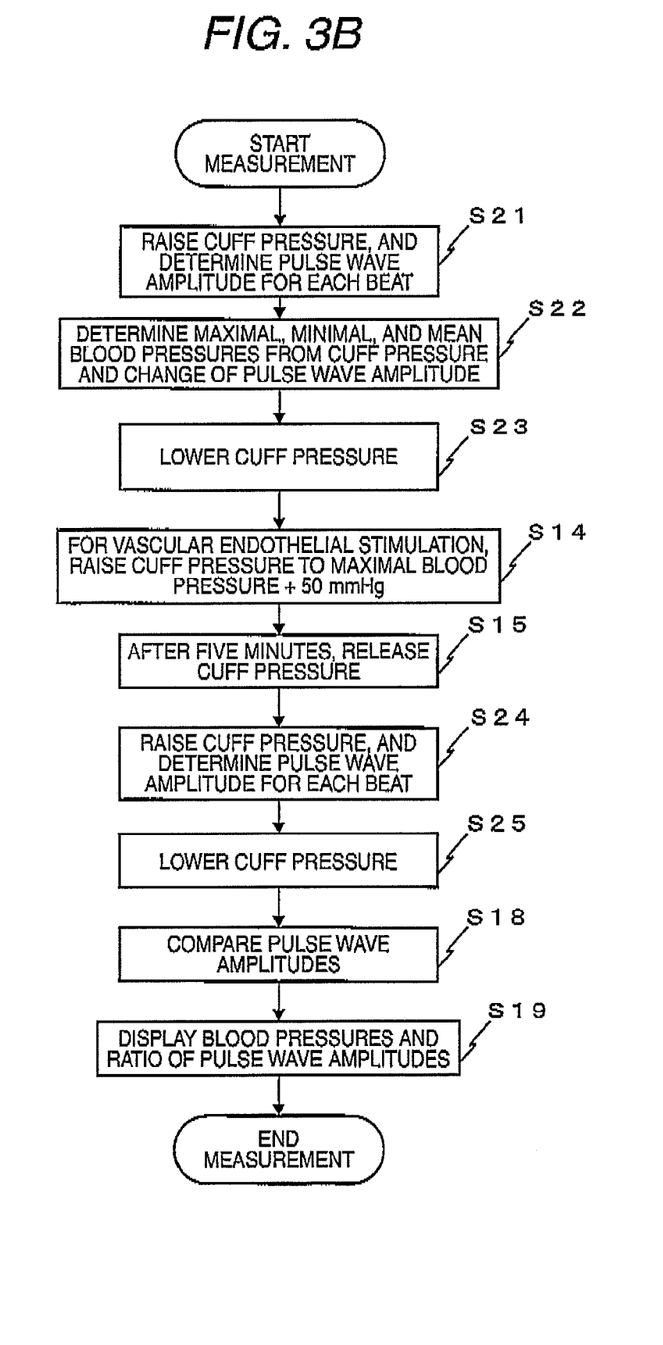
FIG. 3B is a flowchart illustrating a pulse wave measuring operation which is performed in a process of pressurizing the cuff pressure by the embodiment of the apparatus.

In the embodiment, the measurement is performed during the process of depressurizing the cuff pressure. Alternatively, the measurement may be performed during the process of pressurizing the cuff pressure as shown in FIG. 3B. Namely, under the control of the controlling unit 20, in the state where the valve 13 is closed, the air is sent from the pump 12 to the cuff 11 to raise the cuff pressure, and, during the process in which the cuff pressure is raised, the pulse wave detecting unit 32 detects the pulse wave amplitude for each beat (S21).

Figure 3C:
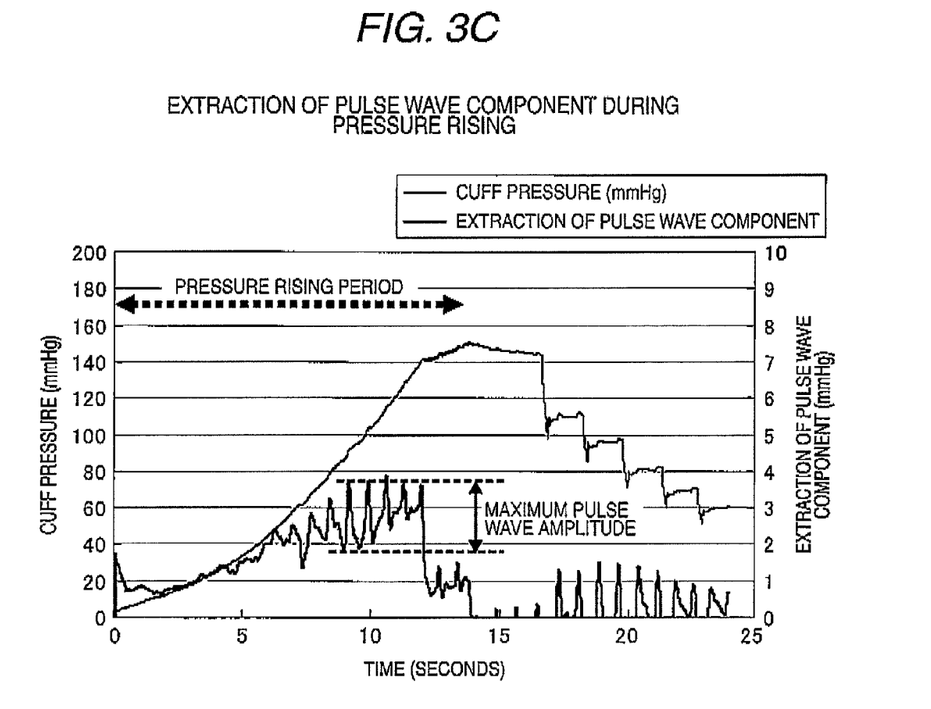
FIG. 3C is a view showing a measurement waveform in the case where the pulse wave measuring operation is performed in the process of pressurizing the cuff pressure by the embodiment of the apparatus.

Furthermore, the cuff pressure detecting unit 31 detects the cuff pressure from the output of the pressure sensor 14, and, on the basis of the cuff pressure and the pulse wave amplitude, the analyzing unit 33 determines the maximal, minimal, and mean blood pressures, and obtains a representative pulse wave amplitude (S22). The representative pulse wave amplitude is obtained by statistically processing the pulse wave amplitude which is obtained in a pressurization period shown in FIG. 3C. The pulse wave amplitude in the pressurization period is obtained as shown in FIG. 3C, and hence the maximum pulse wave amplitude is obtained. In the pressurization period, when the cuff pressure is equal to the mean blood pressure, the pulse wave amplitude is maximum, and the amplitude is set as the maximum pulse wave amplitude.

After the pressurization period which is adequately set as described above, the cuff pressure is lowered (S23), processing in steps S14 and S15 which are identical with that in the embodiment shown in FIG. 3A is performed, and thereafter the cuff pressure is raised. During the process in which the cuff pressure is raised, the pulse wave detecting unit 32 detects the pulse wave amplitude for each beat (S24). The processing of step S24 is identical with that in steps S21 and S22. After the processing, the cuff pressure is lowered (S25), and processing in steps S18 and S19 which are identical with that in the embodiment shown in FIG. 3A is performed.

Figure 4:
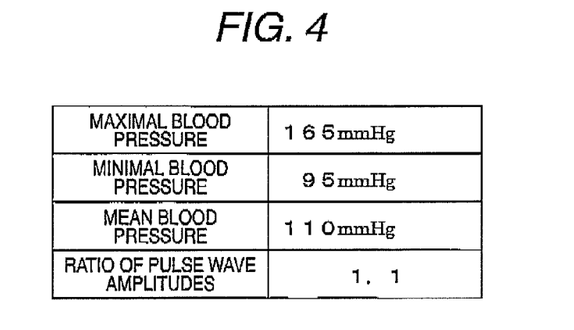
FIG. 4 is a view showing an example of information displayed by the embodiment of the apparatus.
Figure 5:
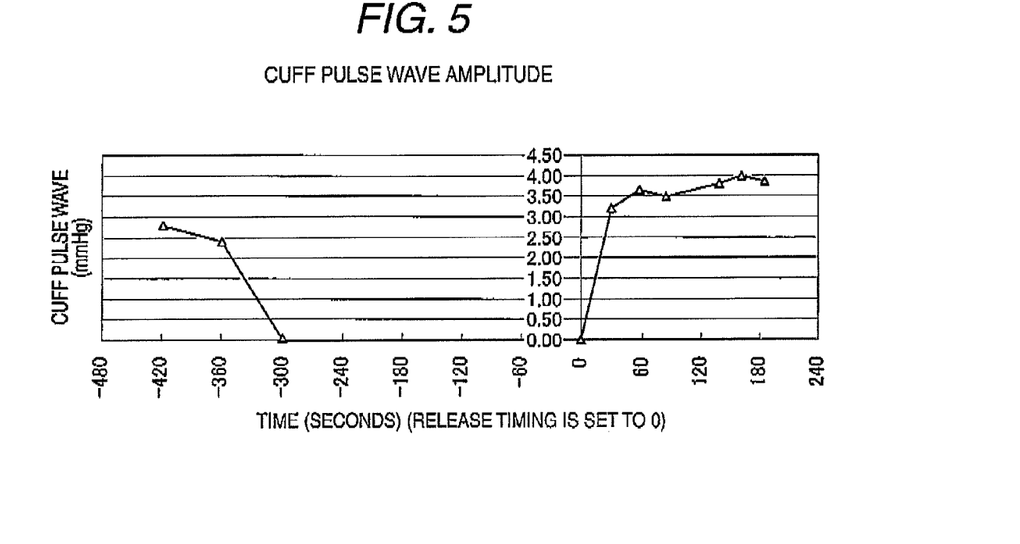
FIG. 5 is a view showing an example of information displayed by the embodiment of the apparatus.
Figure 6:
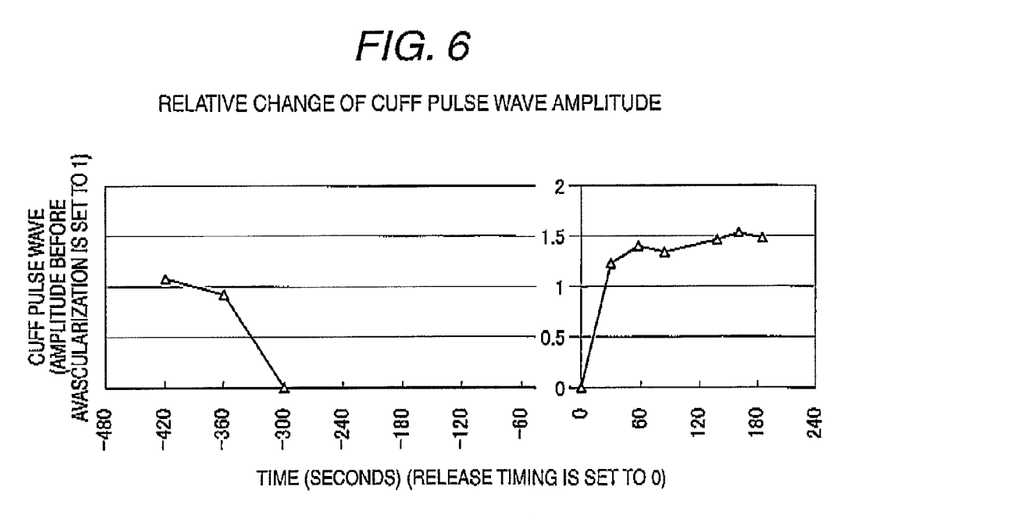
FIG. 6 is a view showing an example of information displayed by the embodiment of the apparatus.
Figure 7:
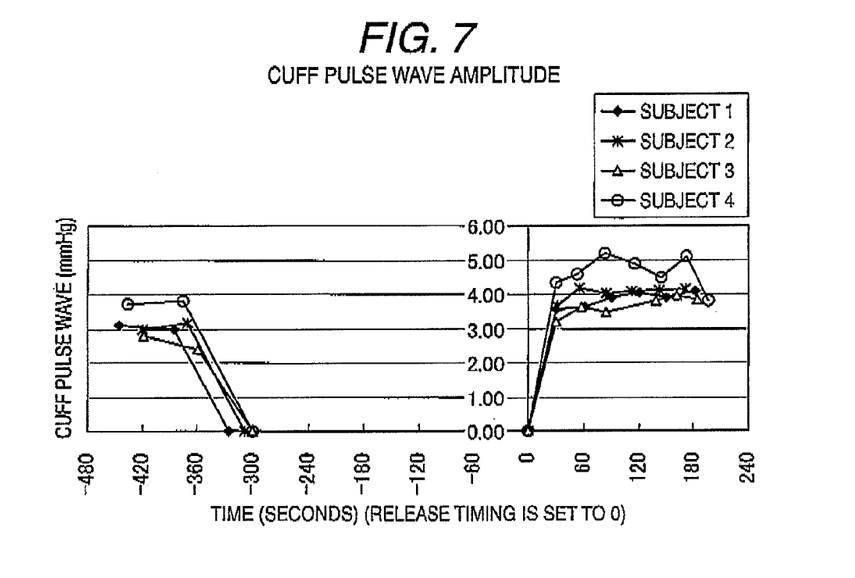
FIG. 7 is a view showing an example of information displayed by the embodiment of the apparatus.
Figure 8:
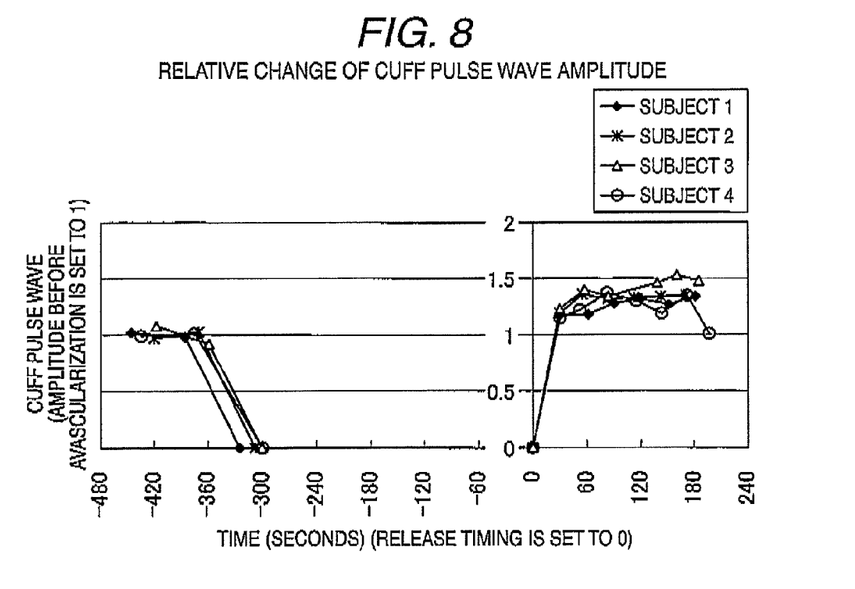
FIG. 8 is a view showing an example of information displayed by the embodiment of the apparatus.

The apparatus for evaluating a vascular endothelial displays the blood pressure values together with a result of a comparison of the pulse wave amplitudes which are obtained as described above, on the displaying unit 40 as shown in FIG. 4. As the blood pressure values, values of a preset one of the pressurization periods Tp and Ta are displayed. The apparatus for evaluating a vascular endothelial may produce a graph which is shown in FIG. 5, and in which the value of the cuff pulse wave amplitude is plotted in time series, and display the graph on the displaying unit 40. Furthermore, the apparatus may produce a graph which is shown in FIG. 6, and in which a ratio of the representative pulse wave amplitude B to the representative pulse wave amplitude A is plotted in time series, and display the graph on the displaying unit 40. The apparatus for evaluating a vascular endothelial may have a storage unit which accumulates data of a plurality of subjects, and display the graphs of FIGS. 5 and 6 of plural subjects in an overlapped manner, as shown in FIGS. 7 and 8.

Figure 9:
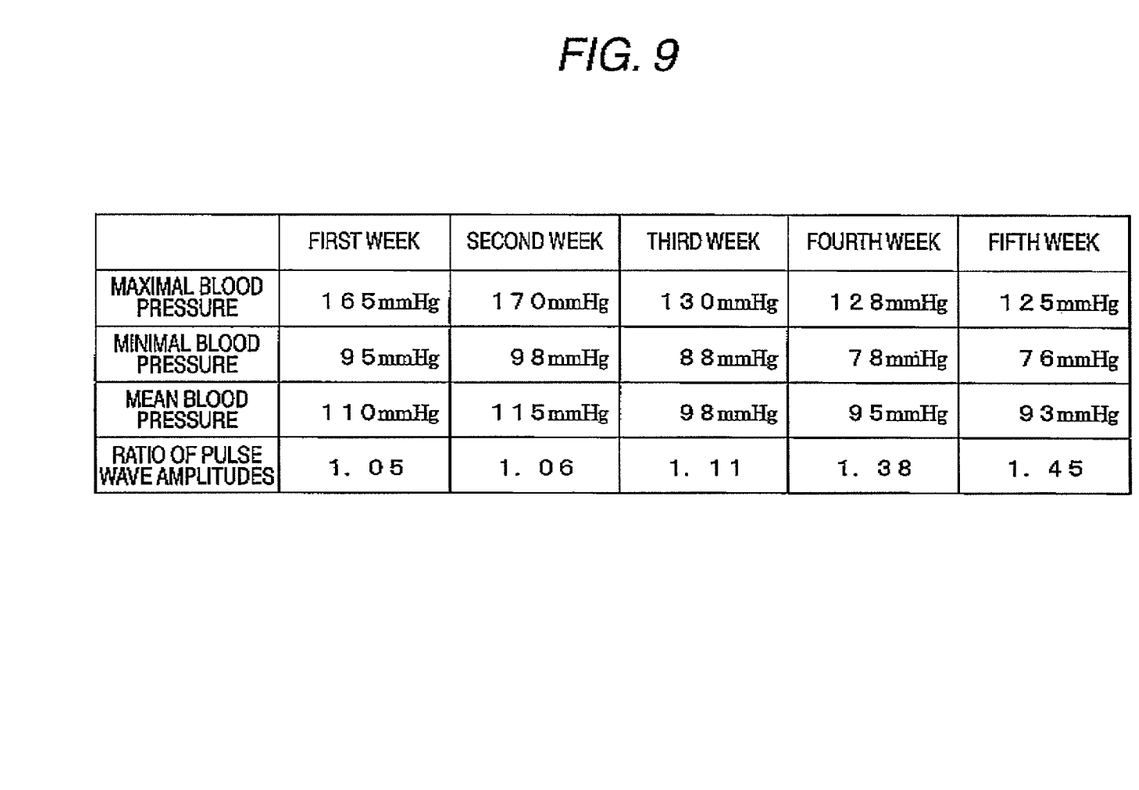
FIG. 9 is a view showing an example of information displayed by the embodiment of the apparatus.
Figure 10:
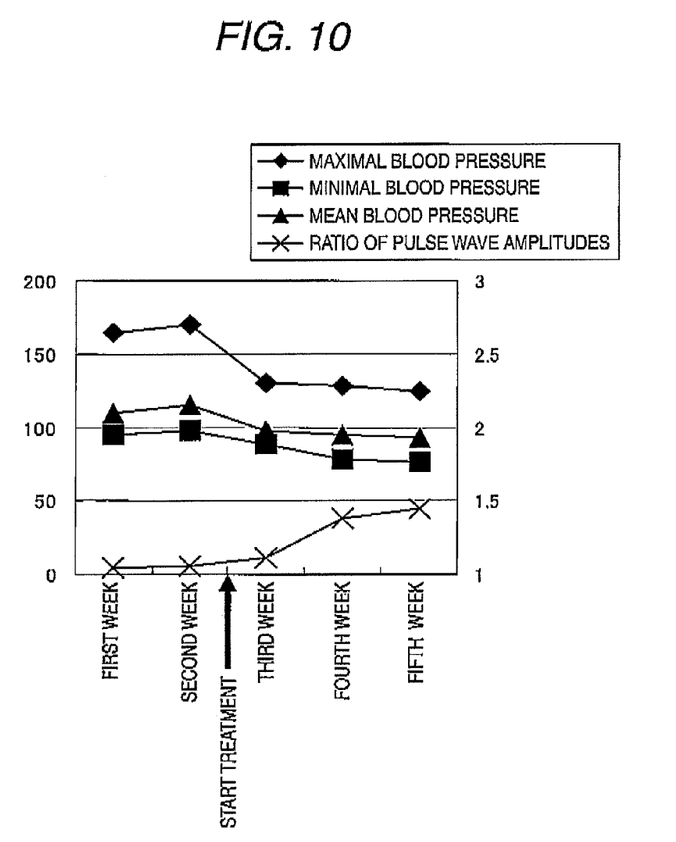
FIG. 10 is a view showing an example of information displayed by the embodiment of the apparatus.

Moreover, history information of measured data may be caused to remain, and the trend may be displayed on the displaying unit 40 in the form of a list as shown in FIG. 9. From the data of the table shown in FIG. 9, the graph shown in FIG. 10 may be produced, and the trend may be displayed on the displaying unit 40. The example of FIGS. 9 and 10 shows data in the case where subjects with high blood pressure were treated after the third week. It is very clear that, after the third week, the blood pressure is lowered and the pulse wave amplitude ratio is improved from "1" to a value in the vicinity of "1.5".

The process in which, as described above, continuous pressure stimulation is performed by the cuff pressure on a part of the body of the subject for a predetermined time means the followings. Normal vascular endothelial cells are caused to produce vasodepressor materials such as nitric monoxide (NO) by stimulation due to a blood flow or medication. When the vascular endothelial function is lowered, the ability of producing vasodepressor materials is lowered. When the degree of vessel expansion by stimulation is measured, therefore, it is possible to evaluate the vascular endothelial function.

The relationships among the inner vascular pressure, the cuff pressure, and the pulse wave amplitude contained in the cuff pressure signal can be described as follows. First, it is known that, when the inner vascular pressure and the cuff pressure are equal to each other, the vascular compliance is maximum. The non-invasive blood pressure measurement by the oscillometric method uses the property. When the cuff pressure is equal to the mean blood pressure, the difference between the maximal and minimal blood pressures in a vessel, i.e., the vessel volumetric change due to the pulse pressure is maximum. Therefore, the maximum pulse wave amplitudes A and B are detected in the pressurization periods Ta and Tp, and set as representative pulse wave amplitudes.

A representative pulse wave amplitude is a pulse wave amplitude under conditions where the relationships between the cuff pressure and the inner vascular pressure are substantially identical with one another in a series of pulse wave amplitude changes. Therefore, pulse wave amplitudes at application of the same predetermined cuff pressure may be employed in place of the maximum pulse wave amplitudes A and B. In any case, a representative pulse wave amplitude can be obtained by statistically processing the pulse wave amplitude which is obtained in the pressurization period.

Figure 11A:
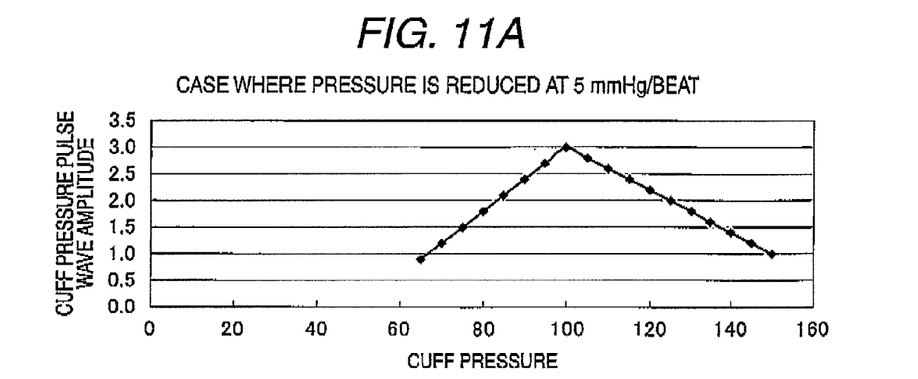
FIGS. 11A to 11C are views illustrating statistical processing which is performed by the embodiment of the apparatus.
Figure 11B:
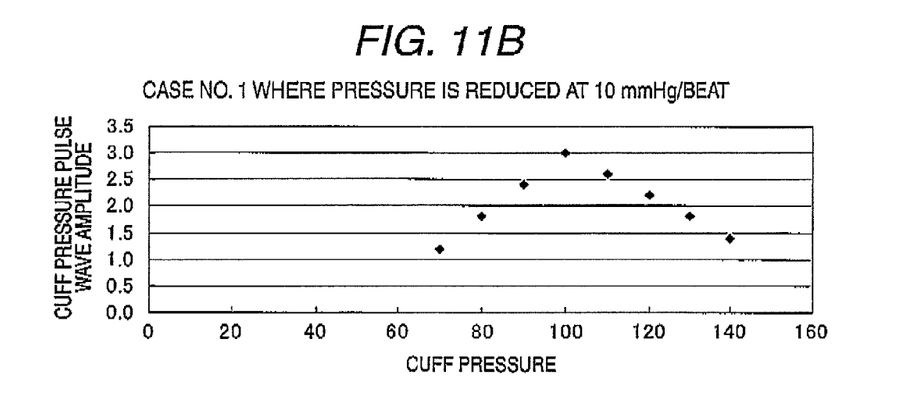
Figure 11C:
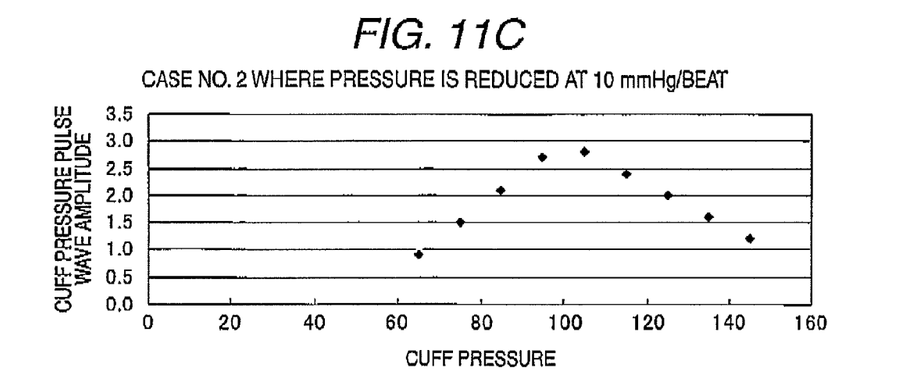

The pulse pressure is repeated due to contraction and expansion of the heart. Therefore, the relationships between the pulse pressure and the change of the cuff pressure are not constant. FIGS. 11A to 11C show relationships between the change of the cuff pressure and the pulse wave amplitude. FIG. 11A shows a pulse wave amplitude in the case where the pressure is reduced at the rate of 5 mmHg per beat, and FIGS. 11B and 11C show a pulse wave amplitude in the case where the reduction rate is increased. In FIGS. 11B and 11C, the relationships between the reduction start timing and the pulse beat are different from each other.

In FIGS. 11B and 11C, the maximum pulse wave amplitudes are 3 mmHg and 2.8 mmHg, respectively, and there is a difference of 0.2 mmHg. The analyzing unit 33 performs statistical processing in which the mean value of pulse wave amplitudes at predetermined number (for example, three) of points in the neighborhood of the maximum pulse wave amplitude is calculated among obtained pulse wave amplitudes. In the example, when the mean value of pulse wave amplitudes at three points is calculated, the obtained mean value in FIG. 11B is 2.67 mmHg, and that in FIG. 11C is 2.64 mmHg. The difference can be reduced. Therefore, it is possible to obtain a value which is preferred as a representative pulse wave amplitude.

In the above description, the pressurization periods Tp and Ta for measuring the pulse wave amplitude are realized before and after the pressurization period T for vascular endothelial stimulation, and one measurement is performed in each of the pressurization periods Tp and Ta for measuring the pulse wave amplitude. Alternatively, a plurality of measurements may be performed. In the alternative, the numbers of measurements before and after the pressurization period may be different from each other.

Figure 12A:
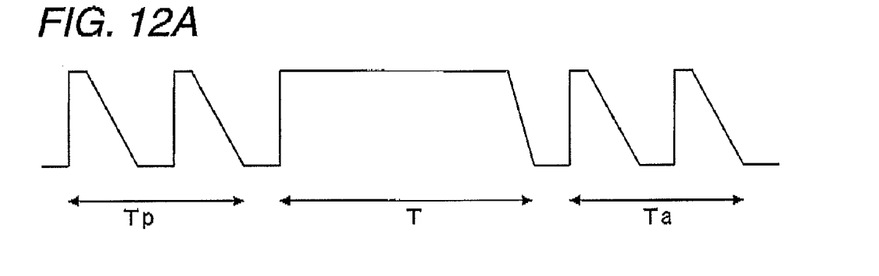
FIGS. 12A and 12B are views showing a second example of the pulse wave measurement which is performed by the embodiment of the apparatus, and the avascularization period.
Figure 12B:
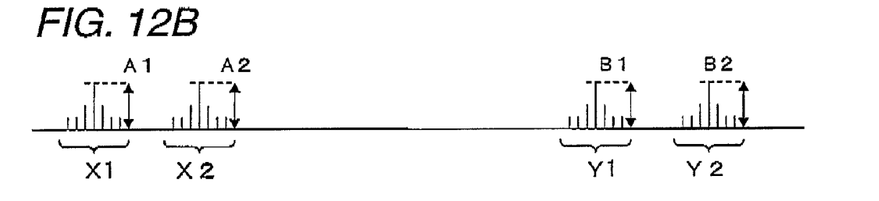

FIGS. 12A and 12B show an example in which two measurements are performed in each of the pressurization periods Tp and Ta. In this example, during the pressurization period Tp, the analyzing unit 33 obtains measured-value groups X1 and X2 as a result of the two measurements. Each of the measured-value groups X1 and X2 is statistically processed to obtain representative pulse wave amplitudes A1 and A2. In this example, maximum pulse wave amplitudes A1 and A2 are obtained as shown in FIG. 12B.

Also during the pressurization period Ta, measured-value groups Y1 and Y2 are obtained as a result of the two measurements. The analyzing unit 33 performs statistical processing on the measured-value groups Y1 and Y2, and obtains maximum pulse wave amplitudes B1 and B2 which are representative pulse wave amplitudes as shown FIG. 12B.

Furthermore, the analyzing unit 33 performs statistical processing for obtaining the respective mean values on the maximum pulse wave amplitudes A1 and A2 and the maximum pulse wave amplitudes B1 and B2, to obtain final representative pulse wave amplitudes. Namely, (A1+A2)/2 and (B1+B2)/2 are obtained as representative pulse wave amplitudes. As a result of the above-described measurements and processing, errors can be leveled, and highly accurate evaluation is enabled.

The mean values of (A1+A2)/2 and (B1+B2)/2 which are obtained as described above are compared with each other by the analyzing unit 33, {(B1+B2)/2}/{(A1+A2)/2} is calculated by means of division, and the calculation result is displayed together with the blood pressure value on the displaying unit 40.

Other measurement technique and statistical processing will be described. The vessel expansion due to vascular endothelial stimulation derived from avascularization by the cuff 11 and its release is gradually increased after the release of the avascularization to reach the peak after several tens of seconds, and thereafter is reduced for several minutes. Based on the peak, it is possible to evaluate the degree of vessel expansion. After the vascular endothelial stimulation, the maximum value of the pulse wave amplitude is measured several times, and a maximum one of the maximum values is set as the pulse wave amplitude in the vessel expansion, thereby obtaining the peak of the vessel expansion.

Figure 13A:
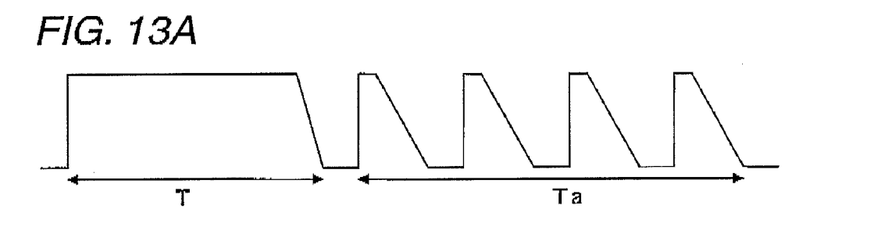
FIGS. 13A to 13C are views showing a third example of the pulse wave measurement which is performed by the embodiment of the apparatus, and the avascularization period.
Figure 13B:
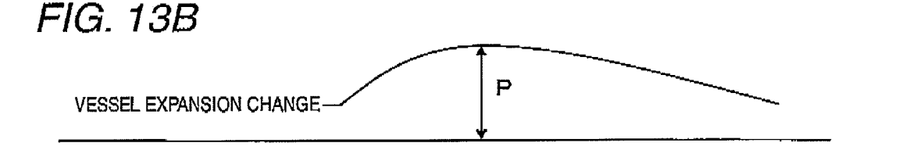
Figure 13C:
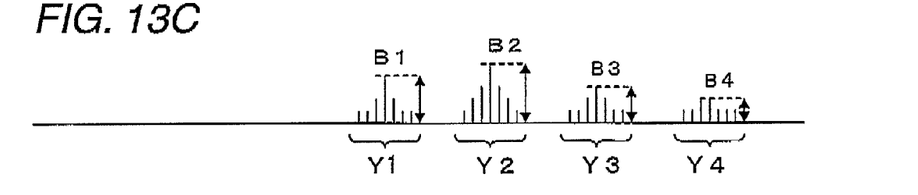

As shown in FIGS. 13A to 13C, specifically, the pressurization period Ta for measuring the pulse wave amplitude is realized after the pressurization period T. In the example, four measurements are performed. As a result of the four measurements, measured-value groups Y1, Y2, Y3, and Y4 are obtained. In this case, the vessel expansion changes as shown FIG. 13B, and it is estimated that a peak P exists in the vicinity of the measured-value group Y2. The analyzing unit 33 performs statistical processing on the measured-value groups Y1, Y2, Y3, and Y4, and, as shown in FIG. 13C, obtains maximum pulse wave amplitudes B1, B2, B3, and B4 which are representative pulse wave amplitudes.

The analyzing unit 33 compares the levels of the maximum pulse wave amplitudes B1, B2, B3, and B4 with one another, and selects the maximum pulse wave amplitude B2 as a representative pulse wave amplitude. The maximum pulse wave amplitude B2 is handled in the same manner as the above-described maximum pulse wave amplitude B. Namely, the amplitude is compared in the analyzing unit 33, and a ratio with respect to the maximum pulse wave amplitude which is obtained by the measurement before the pressurization period T is calculated, and displayed together with obtained blood pressure value on the displaying unit 40.

Finally, the vascular compliance will be described. When V indicates the cuff interior volume, P indicates the cuff internal pressure, and the temperature is assumed to be constant, the following expression holds from the gas state equation:

$$P \times V = \text{constant} = k.$$

Here, transition advances in the sequence of the vascular volume change $\Delta V \to \to$ the cuff volume change of $-\Delta V \to \to$ the pressure change $\Delta P$. Therefore, $$(P+\Delta P) \times (V-\Delta V) = k.$$

When $\Delta P \times \Delta V$ is deemed to be small as compared with the other terms and ignored, $$P \times V + V \times \Delta P - P \times \Delta V = k.$$

Substituting $P \times V = k$, $$V \times \Delta P - P \times \Delta V = 0.$$

$$\Delta V = \Delta P \times V/P \quad \text{(Exp. 1)}$$

Therefore, the cuff pressure change $\Delta P$ is proportional to the vascular volume change $\Delta V$ (in the case where V and P are constants).

It is known that P at which the volume change $\Delta V$ is maximum is the mean blood pressure (because the state where the pressures internal and external of the vessel are balanced with each other is attained). The vascular volume change $\Delta V$ is determined by the pulse pressure $\Delta BP$ (maximal blood pressure−minimal blood pressure) and the vascular compliance C. Namely, following Exp. 2 holds:

$$\Delta V = C \times \Delta BP \quad \text{(Exp. 2)}$$

Here, $\Delta V$ before the pressure stimulation is indicated by $\Delta V1$, $\Delta V$ after the pressure stimulation is indicated by $\Delta V2$, C before the pressure stimulation is indicated by C1, C after the pressure stimulation is indicated by C2, $\Delta P$ before the pressure stimulation is indicated by $\Delta P1$, and $\Delta P$ after the pressure stimulation is indicated by $\Delta P2$. In this case, it is found that the evaluation of the vascular endothelial function can be performed on the basis of the vascular compliance in accordance with following conditions 1 and 2.

Condition 1; the case where the maximal, minimal, and mean blood pressures are not changed before and after the pressure stimulation In the case where, before and after the pressure stimulation, the mean blood pressure is not changed and the cuff attachment state is not changed, P and V of (Exp. 1) are constant. Therefore, a change of $\Delta P$ indicates that of $\Delta V$. In the case where, before and after the pressure stimulation, the maximal and minimal blood pressures are not changed, $\Delta BP$ is constant, and hence the following is attained from (Exp. 2):

$$\Delta P2/\Delta P1 = \Delta V2/\Delta V1 = C2/C1.$$

When cuff pressure pulse waves are compared with each other, it is possible to compare the vascular compliances (softnesses) with each other.

Condition 2: the case where the blood pressure is changed before and after the pressure stimulation It remains unchanged that, when the cuff internal pressure is equal to the mean blood pressure, $\Delta V$ indicates the maximum value. From (Exp. 2), $\Delta V$ is proportional to $\Delta BP$. When $\Delta V/\Delta BP$ is obtained, therefore, it is possible to obtain a more correct vascular compliance C.

The analyzing unit 33 performs processing in which the vascular compliance is obtained, in addition to the processings in which a result of comparison of pulse waves, and blood pressures are obtained. The analyzing unit 33 divides the detected pulse wave amplitude by the difference between the maximal and minimal blood pressures, to obtain the vascular compliance C. As described above, when the inner vascular pressure and the cuff pressure are equal to each other, the vascular compliance is maximum. The compliance which is to be obtained in this case is not restricted to a value when the inner vascular pressure and the cuff pressure are equal to each other. During the pressurization periods Tp and Ta for measuring the pulse wave amplitude which are set before and after the pressurization period T, compliances for representative pulse wave amplitudes which are respectively obtained in the periods may be obtained. The obtained compliances are displayed on the displaying unit 40, independently or together with the ratio of the pulse wave amplitudes which have been described, and obtained blood pressure values. In this case, data of the measured compliances may be caused to remain as history information, the information may be formed as a table or a graph, and the trend may be displayed on the displaying unit 40.

According to an aspect of the invention, by contrast, a change in vascular volume before and after the pressure stimulation is measured, so that information which is equivalent to that obtained in the FMD method that is a reliable related-art technique can be easily obtained, and the measurement can be performed by a technique and configuration which are similar to those of the blood pressure measurement that is currently widely performed, so that skills are not required.

The vessel volumetric change obtained in the present invention is a change of the vascular volume in an area where a cuff is attached. The cuff-attached area is constant in a series of measurements, and hence the vessel volumetric change can be deemed as a change in the vessel sectional area. While a change in vessel diameter is obtained in the FMD method, the square of the vessel diameter can be deemed as the sectional area, and hence a vessel expansion phenomenon which is to be obtained can be detected highly sensitively.

According to an aspect of the invention, an idle period when the cuff pressurization is stopped exists between the pressure stimulation and the pulse wave measurement. Therefore, a continuous vessel blocking period is kept to the minimum, so that the burden on the subject can be reduced.

According to an aspect of the invention, by contrast, the cuff for the pressure stimulation functions also as a sensor for measurement. Therefore, a sensor other than the attachment of the cuff is not necessary, and an additional configuration is not required. Consequently, the present invention is advantageous not only in operation but also in cost.

According to an aspect of the invention, by contrast, it is requested only to measure the amplitude of a pulse wave, and hence an analyzing unit is not required to have a high processing capacity.

The vascular compliance is changed by the blood pressure. When the blood pressure is high, the vessel wall is in a state where the wall is extended in the circumferential direction and hardened, and the compliance is low. Conversely, when the blood pressure is low, a force acting on the vessel wall is small. Therefore, the vessel wall is extended in a smaller degree in the circumferential direction, and the compliance is high. All of the related arts disclosed in JP-A-2007-209492, JP-A-2006-181261, and Japanese Patent No. 3632014 have a problem in that the measured vessel information is inevitably affected by the intravascular pressure, i.e., the blood pressure.

It is known that the cuff pressure indicating the maximum pulse wave amplitude corresponds to the mean blood pressure. Irrespective of the level of the blood pressure, when a vessel is compressed by a cuff at a pressure which is equal to the mean blood pressure, the pressures internal and external of the vessel counteract each other, and the force acting in the circumferential direction of the vessel wall is minimized. The maximum pulse wave amplitude which is measured in the present invention is always measured in a state where the force acting in the circumferential direction of the vessel wall is minimum, and therefore the influence of the level of the blood pressure on the measurement result is reduced. In the present invention, the maximum pulse wave amplitude in the case where the cuff pressure is changed is measured, whereby the influence of the blood pressure can be reduced.

According to an aspect of the invention, continuous pressure stimulation is performed on a part of the body of the subject for a predetermined time, and the analyzing unit evaluates the vascular endothelial function by comparing pulse waves detected before and after the pressure stimulation is applied. Therefore, the configuration and the measurement technique are simplified, and, since the pulse waves detected before and after the pressure stimulation is applied are proportional to the vessel volumetric change, the comparison of the pulse waves enables the evaluation of the vascular endothelial function to be performed highly accurately.

Related-art blood pressure measurement involves compression which is performed on the subject by a cuff for several tens of seconds. According to an aspect of the invention, the blood pressure measurement is performed during the process of pressurizing the cuff pressure, and hence the measurement is completed during the process in which the subject is compressed. Therefore, the measurement time can be shortened, and the burden on the subject can be reduced.

According to an aspect of the invention, the blood pressure measurement is performed during the process of pressurizing the cuff pressure, and hence the influence which is exerted on the vascular response by avascularization can be reduced to the minimum.

What is claimed is:

1. An apparatus for evaluating a vascular endothelial function, the apparatus comprising:
    a cuff, to be wound around a part of a body of a subject;
    a cuff pressure controller, configured to control a pressure of the cuff during a first pressurization period in which the cuff is pressurized and depressurized for performing first blood pressure measurement, configured to control the pressure of the cuff and apply continuous pressure stimulation during a continuous pressure stimulation period, and configured to control the pressure of the cuff during a second pressurization period in which the cuff is pressurized and depressurized for performing second blood pressure measurement;
    a cuff pressure detector, configured to detect the pressure of the cuff from output of a pressure sensor connected to the cuff;
    a pulse wave detector, configured to detect, from the output of the pressure sensor, first pulse waves during the first pressurization period before the continuous pressure stimulation during the continuous pressure stimulation period is applied and second pulse waves during the second pressurization period after the continuous pressure stimulation during the continuous pressure stimulation is applied; and
    an analyzer, configured to evaluate the vascular endothelial function by comparing the first pulse waves and the second pulse waves.

2. The apparatus according to claim 1, wherein the analyzer obtains an amplitude ratio between the first pulse waves and the second pulse waves.

3. The apparatus according to claim 1, wherein the continuous pressure stimulation is a constant pressure for a time period.

4. The apparatus according to claim 1, wherein the cuff pressure controller is configured to control the pressure of the cuff during the continuous pressure stimulation period by raising the pressure of the cuff from a first pressure which is an atmosphere pressure to a second pressure, applying the continuous pressure stimulation at the second pressure for a predetermined time period, and lowering the pressure of the cuff from the second pressure to a third pressure, and
    wherein the analyzer applies statistical processing on the first pulse waves and the second pulse waves.

5. The apparatus according to claim 4, wherein the statistical processing is processing in which a first maximum amplitude among amplitudes of the first pulse waves detected in the first pressurization period is obtained and a second maximum amplitude among amplitudes of the second pulse waves detected in the second pressurization period is obtained.

6. The apparatus according to claim 4, wherein the statistical processing is processing in which a first average value of amplitudes of the first pulse waves that are in proximity in time to a first pulse wave having a maximum amplitude is obtained and a second average value of amplitudes of the second pulse waves that are in proximity in time to a second pulse wave having a maximum amplitude is obtained.

7. The apparatus according to claim 4, wherein the second pressure is equal to or greater than a maximal blood pressure of the subject, and
    the third pressure is equal to or less than a minimal blood pressure of the subject.

8. The apparatus according to claim 1, wherein the analyzer performs processing in which an amplitude of each of the first pulse waves is divided by a difference between a first maximal blood pressure of the subject during the first pressurization period and a first minimal blood pressure of the subject during the first pressurization period and an amplitude of each of the second pulse waves is divided by a difference between a second maximal blood pressure of the subject during the second pressurization period and a second minimal blood pressure of the subject during the second pressurization period, to obtain vascular compliance.

9. The apparatus according to claim 1, further comprising a display, wherein the analyzer calculates at least one of a maximal blood pressure, a minimal blood pressure, and a mean blood pressure from amplitudes of at least one of the first pulse waves and the second pulse waves, and the display displays the at least one of the maximal blood pressure, the minimal blood pressure, and the mean blood pressure together with a comparison result of the first pulse waves and the second pulse waves.

10. A method of evaluating a vascular endothelial function by an apparatus, configured to control a pressure of a cuff to be wound around a part of a body of a subject and configured to detect the pressure of the cuff from output of a pressure sensor connected to the cuff, the method comprising;
    applying first pressurization during a first pressurization period in which the cuff is pressurized and depressurized for performing first blood pressure measurement, continuous pressure stimulation during a continuous pressure stimulation period, and second pressurization during a second pressurization period in which the cuff is pressurized and depressurized for performing second blood pressure measurement;

detecting, from the output of the pressure sensor, first pulse waves during the first pressurization period before the continuous pressure stimulation during the continuous pressure stimulation period is applied and second pulse waves during the second pressurization period after the continuous pressure stimulation during the continuous pressure stimulation is applied; and evaluating, by a processor of the apparatus, the vascular endothelial function by comparing the first pulse waves and the second pulse waves.

11. The method according to claim 10, wherein the vascular endothelial function is evaluated by obtaining an amplitude ratio between the first pulse waves and the second pulse waves.

12. The method according to claim 10, wherein the continuous pressure stimulation is a constant pressure for a time period.

13. The method according to claim 10, wherein applying the continuous pressure stimulation during the continuous pressure stimulation period comprises:

raising the pressure of the cuff from a first pressure which is an atmosphere pressure to a second pressure;

applying the continuous pressure stimulation at the second pressure for a predetermined time period; and lowering the pressure of the cuff from the second pressure to a third pressure, and wherein the evaluating comprises applying statistical processing on the first pulse waves and the second pulse waves.

14. The method according to claim 13, wherein the statistical processing is processing in which a first maximum amplitude among amplitudes of the first pulse waves detected in the first pressurization period is obtained and a second maximum amplitude among amplitudes of the second pulse waves detected in the second pressurization period is obtained.

15. The method according to claim 13, wherein the second pressure is equal to or greater than a maximal blood pressure of the subject, and the third pressure is equal to or less than a minimal blood pressure of the subject.

16. The method according to claim 13, wherein the statistical processing is processing in which a first average value of amplitudes of the first pulse waves that are in proximity in time to a first pulse wave having a maximum amplitude is obtained and a second average value of amplitudes of the second pulse waves that are in proximity in time to a second pulse wave having a maximum amplitude is obtained.

17. The method according to claim 10, further comprising:

performing processing in which an amplitude of each of the first pulse waves is divided by a difference between a first maximal blood pressure of the subject during the first pressurization period and a first minimal blood pressure of the subject during the first pressurization period and an amplitude of each of the second pulse waves is divided by a difference between a second maximal blood pressure of the subject during the second pressurization period and a second minimal blood pressure of the subject during the second pressurization period, to obtain vascular compliance.

18. The method according to claim 10, further comprising:

calculating at least one of a maximal blood pressure, a minimal blood pressure, and a mean blood pressure from amplitudes of at least one of the first pulse waves and the second pulse waves; and displaying the at least one of the maximal blood pressure, the minimal blood pressure, and the mean blood pressure together with a comparison result of the first pulse waves and the second pulse waves.

* * * * *